United States Patent [19]

Smith et al.

[11] 4,130,009
[45] Dec. 19, 1978

[54] METHOD AND APPARATUS FOR DETERMINING THERMOPARTICULATION TEMPERATURE OF COMPOUNDS

[75] Inventors: James D. B. Smith, Turtle Creek; David C. Phillips, Pittsburgh, both of Pa.

[73] Assignee: Westinghouse Electric Corp., Pittsburgh, Pa.

[21] Appl. No.: 769,130

[22] Filed: Feb. 16, 1977

Related U.S. Application Data

[62] Division of Ser. No. 669,554, Mar. 23, 1976, Pat. No. 4,102,809, which is a division of Ser. No. 390,284, Aug. 21, 1973, Pat. No. 3,973,438.

[51] Int. Cl.² ............................................. G01N 25/02
[52] U.S. Cl. .................................. 73/17 R; 73/339 R; 116/114 Y
[58] Field of Search ............. 73/356, 15 R, 28, 339 R, 73/1 F, 17 R; 250/83.6, 383; 356/43; 340/273 R; 116/114 Y

[56] References Cited

U.S. PATENT DOCUMENTS

| | | | |
|---|---|---|---|
| 3,025,263 | 3/1962 | Lee, Jr. | 260/37 EP X |
| 3,386,807 | 6/1968 | Edenbaum | 73/356 X |
| 3,427,880 | 2/1969 | Grubel et al. | 73/339 R |
| 3,573,460 | 4/1971 | Skala | 250/83.6 |
| 3,684,737 | 8/1972 | Emigh | 73/356 X |
| 3,695,848 | 10/1972 | Taguchi | 340/237 R |
| 3,702,561 | 11/1972 | Carson et al. | 73/1 F |
| 3,720,935 | 3/1973 | Tomlin, Jr. | 340/248 R |
| 3,807,218 | 4/1974 | Carson et al. | 73/28 |
| 3,973,438 | 8/1976 | Smith et al. | 252/408 X |
| 3,995,489 | 12/1976 | Smith et al. | 252/408 X |

FOREIGN PATENT DOCUMENTS

2122385  11/1972  Fed. Rep. of Germany ........ 73/339 R

OTHER PUBLICATIONS

Murphy, C. B., "TPA-A New . . . Materials", Plastics Design & Processing-Reprint, Jul. 1964, pp. 1-4.

Primary Examiner—Daniel M. Yasich
Attorney, Agent, or Firm—R. D. Fuerle

[57] ABSTRACT

A composition is disclosed of malonic acid, a resinous carrier, and a solvent. The composition is applied to a portion of an electrical apparatus which is exposed to a fluid stream. The solvent in the composition is evaporated to produce a thermo-particulating coating. When the electrical apparatus overheats the malonic acid in the coating forms particles in the fluid stream which are detected by a monitor.

14 Claims, 1 Drawing Figure

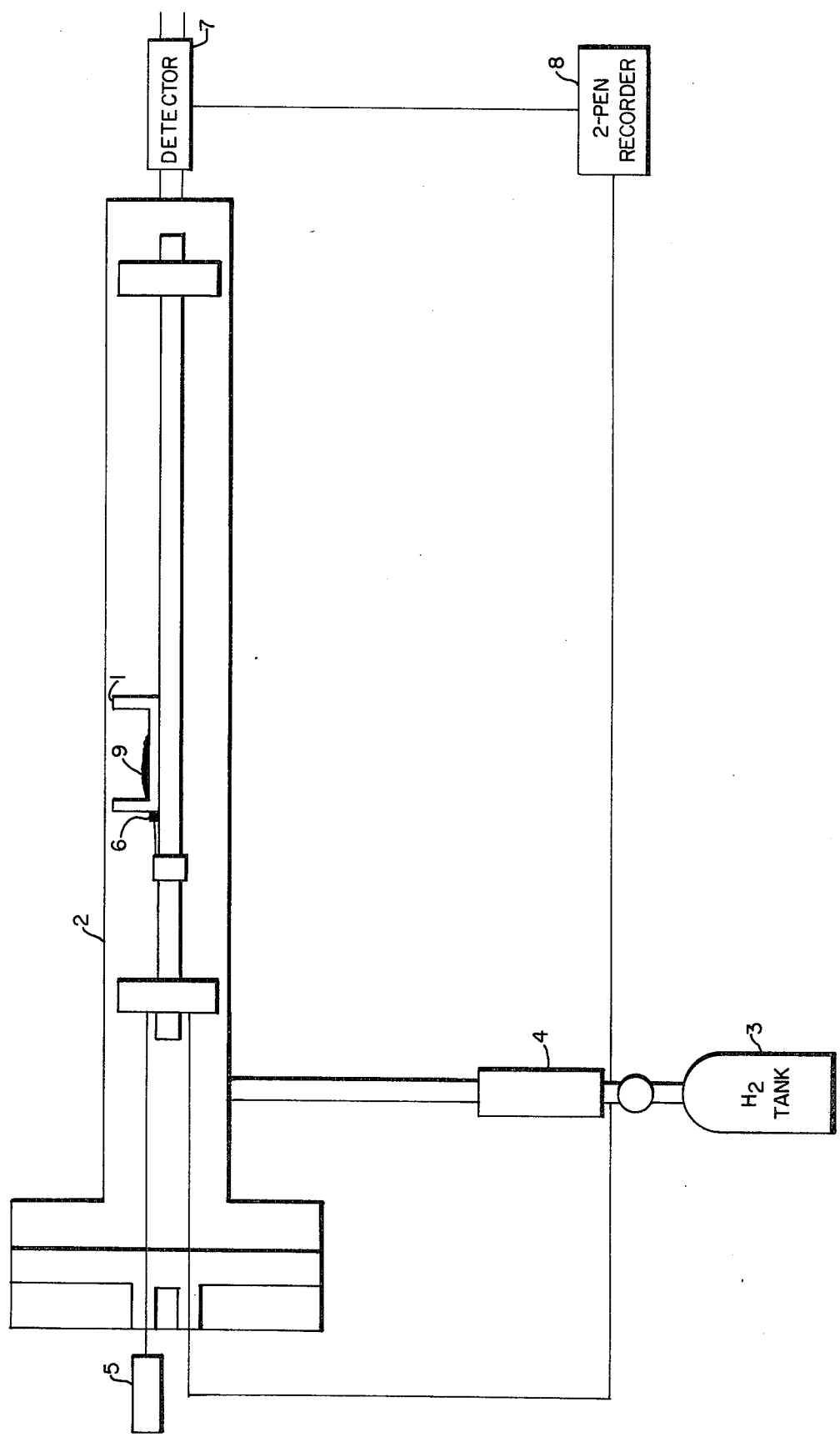

METHOD AND APPARATUS FOR DETERMINING THERMOPARTICULATION TEMPERATURE OF COMPOUNDS

This application is a division of application Ser. No. 669,554 filed Mar. 23, 1976, now U.S. Pat. No. 4,102,809 which in turn is a division of application Ser. No. 390,284 filed Aug. 21, 1973, now U.S. Pat. No. 3,973,438.

BACKGROUND OF THE INVENTION

Electrical apparatus, such as motors and turbine generators, occasionally overheat due to shorts or other malfunctions. The longer the overheating continues the more damage is done to the apparatus. A malfunction detected immediately may mean only a quick repair but if the overheating continues the entire machine may be damaged.

Large rotating electrical apparatus is usually cooled with a hydrogen gas stream. The organic compounds in the apparatus are first to be affected by the overheating and they decompose to form particles which enter the gas stream. Monitors then detect particles in the gas stream and sound a warning or shut down the apparatus when too many particles are detected.

Descriptions of such monitors and how they function may be found in U.S. Pat. No. 3,427,880 titled "Overheating Detector For Gas Cooled Electrical Machine" and in U.S. Pat. No. 3,573,460 titled "Ion Chamber For Submicron Particles." Another monitor, "The Condensation Nuclei Detector," is described by F. W. Van-Luik, Jr. and R. E. Rippere, in an article titled "Condensation Nuclei, A New Technique For Gas Analysis," in Analytical Chemistry 34, 1617 (1962) and by G. F. Skala, in an article titled "A New Instrument For The Continuous Detection Of Condensation Nuclei," in Analytical Chemistry 35, 702 (1963). As U.S. Pat. No. 3,427,880 suggests, special coatings may be applied to the apparatus which decompose and form detectible particles at a lower temperature than the usual organic compounds found in the apparatus. For example, that patent mentions polyalphamethylstyrene, polystyrene, polymethyl methacrylate, and cellulose propionate which decompose to form particles at 230° to 340° C.

Unfortunately, since these machines normally operate at about 80° to 100° C., they may be severely damaged by the time the temperature reaches 230° to 340° C.

Efforts to identify materials which will decompose to form detectable particles (i.e., thermo-particulate) at temperatures closer to the operating temperature of the machine have met with several difficulties. Many compounds, such as succinic acid, maleic acid, fumaric acid, and polyacrylic acid, do not decompose below 190° C. Others, such as acetic acid, are liquids which boil and therefore are unsuitable. Some compounds, such as oxalic acid, decompose at a low temperature but the decomposition products do not include detectable particles. Compounds such as 1,2-diformylhydrazine have some of the desirable properties but cannot withstand several years operation at 80° to 100° C. A few compounds, such as p-diethylaminobenzene diazonium fluoroborate contain toxic or corrosive substances in their decomposition products which render them unsuitable.

PRIOR ART

A book titled "Chemistry of Carbon Compounds" by E. H. Rodd, Vol. 1, page 962 states that malonic acid decomposes at 130° C. to give carbon dioxide and acetic acid.

SUMMARY OF THE INVENTION

We have found that malonic acid can be used in a composition to form a thermo-particulating coating which produces detectable particles at about 125° C. or less. The coating can be made compatible with the other organic compounds in the apparatus. The coating is very stable and can withstand several years operation at 80° to 100° C. without decomposing, yet still produce detectable particles when the temperature reaches about 125° C. The decomposition products are neither toxic nor corrosive.

We have also found that when the coating is heated to about 125° C. it blisters and becomes a very dark brown color which is a considerable aid in locating the malfunction.

The accompanying drawing is a diagrammatic view of a certain presently preferred embodiment of an apparatus used to determine the temperature at which a compound thermoparticulates.

DESCRIPTION OF THE INVENTION

A composition is prepared of the malonic acid in a solution of a resinous carrier. The malonic acid may be dispersed if it is insoluble in the solvent (e.g., toluene) or it may be in solution if it is soluble in the solvent (e.g., ethyl alcohol or diethyl ether). Dispersions are preferred as they produce much more particulation than do solutions. A particle size of the dispersed malonic acid of about 25 to about 1000 microns is suitable.

A suitable composition is a resinous carrier, about 20 to about 250 phr (parts by weight per hundred parts of resinous carrier) of malonic acid, and about 25 to about 75% (by weight based on the resinous carrier) of a solvent for the resinous carrier. If the amount of malonic acid is less than about 20 phr, the quantity of particles given off during decomposition may be too low to be detected by presently-existing detectors. However, the construction of more sensitive detectors would permit a lower amount of malonic acid. If the amount of malonic acid exceeds about 250 phr the composition is thick, difficult to apply, and does not bond well. The preferred malonic acid amount, which generally gives the best results, is about 40 to about 60 phr. If the amount of solvent is less than about 25% the composition is generally too viscous to apply easily and if the amount of solvent is greater than about 75% the composition is unnecessarily dilute and the coating may be too thin to produce an adequate number of particles during decomposition, at least while the malfunction is highly localized. Best results are usually obtained with about 45 to about 55% solvent.

The composition also preferably contains about 0.1 to about 3 phr of a drier when the resinous carrier is an epoxy resin or similar resin, to promote its room temperature cure. Lead naphthenate or cobalt naphthenate is preferred although stannous octoate, zinc sterate, etc. could also be used. Resins such as polyesters may also require the presence of an organic peroxide as is known in the art. Mixtures of resins, solvents, or driers are also contemplated.

The composition may be prepared by simply mixing the ingredients, but it is preferable to mix the drier, resinous carrier, and solvent first and then add the malonic acid to prevent the occlusion of the drier in the malonic acid and thereby obtain a more homogeneous dispersion of the malonic acid. The composition is applied to portions of the electrical apparatus which are exposed to the fluid stream. The application may be made by painting, spraying, dipping, grease gun, or other techniques. A suitable coating thickness (after drying) is about 1/16 to about ¼ inch. The dispersed malonic acid particles should not be covered with excessive resinous carrier as that may prevent the decomposition particles from escaping into the fluid stream. After evaporation of the solvent and room temperature cure of the resinous carrier, if necessary, the apparatus is ready to be operated.

The resinous carrier performs the function of bonding the malonic acid to the apparatus since a coating of malonic acid by itself does not adhere well. The resinous carrier should be compatible with the other resins used in the apparatus and therefore it is usually advantageous to use the same resin used elsewhere. The resinous carrier should be stable for several years at the operating temperature of the apparatus (80° to 100° C.) and should be air-dryable since it cannot be easily cured in place with heat. Epoxy resins are preferred as they are usually used elsewhere in the apparatus, but polyesters, silicone rubber, styrene, etc. could also be used.

The solvent for the resinous carrier depends on the particular resinous carrier used. Toluene, xylene, benzene, methyl ethyl ketone, ethyl alcohol, diethyl ether, acetone, cellosolve, etc. are common solvents that may be used. Toluene is preferred as it is inexpensive and dissolves most resins.

The following example further illustrates this invention.

EXAMPLE

The following composition was prepared:

|  |  | Parts by Weight |
|---|---|---|
| malonic acid ($CH_2(COOH_2)$) |  | 20 |
| epoxy resin made from 200 phr linseed fatty acids, 200 phr styrene, and 300 phr diglycidyl ether of Bisphenol A. Sold by Westinghouse Electric Corporation as "B-276" Varnish (See Example I of U.S. Pat. No. 2,909,497 for detailed description) |  | 50 |
| 6% solution in low boiling hydrocarbons of cobalt naphthenate |  | 1.0 |
| 24% solution in low boiling hydrocarbons of lead naphthenate |  | 0.25 |
| toluene |  | 50 |

Samples were prepared by brushing the above composition onto ¼ by ½ inch aluminum and copper sheet 1/16 to ¼ inches thick. Also, a sample of polyethylene terephthalate (Dacron) felt (which does not thermoparticulate) was immersed into a 20% methanol solution of malonic acid. The samples were dried to from coatings ¼ inches thick, then placed in an oven at 80° C. for various periods to determine if they were stable and would function after aging.

Referring to the drawing, the samples 1 were placed one at a time in a stainless boat 2 within a 1 inch stainless steel tube 3. Hydrogen from tank 4 was passed through flow meter 5 than over the sample 1 at flow rate of 7 l/min. A phase controlled temperature regulator and programmer 6 controlled the temperature in the boat and the temperature in the boat was measured by mounting a hot junction Chromel-Alumel thermocouple 7 within a small hole in the boat. The output of the thermocouple and the detector 8 were monitored on a two pen potentiostatic recorder 9. A 5° C./min. heating rate was maintained in each experiment after the insertion of the malonic acid sample 1 in the boat. The threshold temperature at which considerable particulation occurred was taken from the chart produced by the recorder. The occurrence of particulation was detected using a Generator Condition Monitor or a condensation nuclei monitor. Both instruments are sold by Environment One Corporation.

The following table gives the results:

| Carrier or Support Material | Sample Heat Treatment | Thermo-Particulation Temperature (° C) | Sample Appearance | |
|---|---|---|---|---|
|  |  |  | Initial | After Particulation |
| Dacron Felt | None | 117° C | White Felt | Dark brown spots within felt |
| " | 7 days at 80° C | 125° C | " | " |
| " | 20 days at 80° C | 125° C | " | " |
| 20% in B-276 varnish on aluminum | 16 hours at 80° C | 117° C | White powder within a yellow matrix | Dark brown craters on varnish surface |
| " | 7 days at 80° C | 125° C | " | " |
| " | 15 days at 80° C | 125° C | " | " |
| 20% in B-276 varnish on copper | 7 days at 80° C | 125° | " | " |
| " | 20 days at 80° C | 125° | " | " |

The table shows that the thermo-particulating temperature is about 125° C. in almost every case and the coating is not affected by the aging period or by copper or aluminum.

In other tests the coatings have remained stable and have thermo-particulated after 6 weeks at 80° C. Samples have also thermo-particulated after aging at 100° C.

We claim:

1. A method of determining the thermoparticulating temperature of a compound which thermoparticulates at a temperature below 230° C. comprising
    (1) mixing about 20 to about 250 phr of said compound into a liquid resin which is unreactive with said compound and which is solidifiable and stable at the thermoparticulating temperature of said compound;
    (2) solidifying said resin;
    (3) providing a flow of gas over said mixture;
    (4) monitoring said gas for the presence of particles therein;
    (5) gradually heating said mixture; and
    (6) noting the temperature of said mixture when said monitor detects particles in said gas.

2. A method according to claim 1 wherein said gas is hydrogen.

3. A method according to claim 1 wherein said monitoring is performed by an ion chamber.

4. A method according to claim 1 wherein said resin is air-dryable.

5. A method according to claim 1 wherein said resin is an epoxy resin.

6. A method according to claim 1 wherein the amount of said compound is about 40 to about 60 phr.

7. A method according to claim 1 wherein said resin is in a solution of a solvent, and the solvent is evaporated to solidify the resin.

8. Apparatus for determining the thermoparticulation temperature of a compound which thermoparticulates at a temperature below 230° C. comprising
(1) a liquid resin which is unreactive with said compound and which is solidifiable and stable at the thermoparticulation temperature of said compound;
(2) means for mixing said liquid resin with about 20 to about 250 phr of said compound and for thereafter solidifying said resin;
(3) means for providing a flow of gas over said mixture;
(4) means for monitoring the presence of particles in said gas;
(5) means gradually heating said mixture; and
(6) means for determining the temperature of said mixture.

9. Apparatus according to claim 8 wherein said gas is hydrogen.

10. Apparatus according to claim 8 wherein said means for monitoring is an ion chamber.

11. Apparatus according to claim 8 wherein said resin is air-dryable.

12. Apparatus according to claim 11 wherein said resin is an epoxy resin.

13. Apparatus according to claim 8 wherein the amount of said compound is about 40 to about 60 phr.

14. Apparatus according to claim 8 wherein said resin is in a solution of a solvent, and the solvent is evaporated to solidify the resin.

* * * * *